United States Patent [19]
Benetti et al.

[11] Patent Number: 5,856,358
[45] Date of Patent: Jan. 5, 1999

[54] MONO- AND DISULFO-SUBSTITUTED ANTHRAQUINONES AND THEIR USE FOR THE TREATMENT OF BONE MATRIX DISORDERS

[75] Inventors: Dino Benetti; Ruggero Aloisi; Giuseppe Guainai; Sergio Rosini, all of Pisa, Italy

[73] Assignee: Boonville Limited, Tortola, Virgin Islands (Br.)

[21] Appl. No.: 981,287

[22] PCT Filed: Jun. 17, 1996

[86] PCT No.: PCT/EP96/02597

§ 371 Date: Jan. 29, 1998

§ 102(e) Date: Jan. 29, 1998

[87] PCT Pub. No.: WO97/00675

PCT Pub. Date: Jan. 9, 1997

[30] Foreign Application Priority Data

Jun. 23, 1995 [IT] Italy .................. Mi95 A 001357

[51] Int. Cl.$^6$ ...................................... A01N 37/12
[52] U.S. Cl. .................... 514/563; 552/208; 552/222
[58] Field of Search ..................... 552/208, 222; 514/563

[56] References Cited

FOREIGN PATENT DOCUMENTS 2025954  1/1980  United Kingdom .
92/16496 10/1992  WIPO .

OTHER PUBLICATIONS

J. Med. Chem., vol. 17, No. 8, 1974, pp.890–893, XP000608424, J. M. Grisar et al, "Bis–basic–substituted polycyclic aromatic compounds. A new class of antiviral agents."

*Primary Examiner*—Gary Geist
*Assistant Examiner*—Sreeni Padmanabhan
*Attorney, Agent, or Firm*—Griffin, Butler, Whisenhunt & Szipl, LLP

[57] ABSTRACT

Compounds of formula (I) for treatment of pathologies in which erosion of cartilaginous and bone matrix occurs, for example osteoarthrosis. An exampliary compound is 2,6-anthraquinonesulfonamido-N,N-caproic acid.

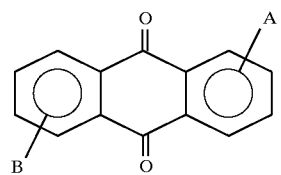

7 Claims, No Drawings

MONO- AND DISULFO-SUBSTITUTED ANTHRAQUINONES AND THEIR USE FOR THE TREATMENT OF BONE MATRIX DISORDERS

This is the U.S. National Stage Application of PCT/EP96/02597 filed Jun. 17, 1996 now WO/97/00875 published Jan. 9, 1997.

The present invention relates to compounds useful for the treatment of the pathologies in which the erosion of the cartilaginous and bone matrix occurs in the most advanced steps of the disease, such as osteoarthrosis and rheumatoid arthritis, and to pharmaceutical compositions containing them. Furthermore, the invention relates to novel anthraquinone derivatives and to the process for the preparation thereof.

Osteoarthrosis are known to be treated mainly using substances acting on the pain and exerting their symptomatic effect thanks to their antiinflammatory activity. Said medicaments are usually referred to as non steroidal antiinflammatory drugs (NSAID) such as for example indomethacin and steroidal ones, such as hydrocortisone and bethametasone.

Other used compounds comprise copper chelating agents, such as penicillamine, and those compounds which interfere with collagene synthesis, with DNA or with synovial membranes, such as cyclophosphamide.

Among the most recent substances used in the above mentioned pathologies there are diacetylrhein, a pro-drug of rhein, which exerts its therapeutical activity being a copper chelating agent, moreover it inhibits the formation of ceruloplasmin during the acute phase of arthritis inflammation and it is also a calcium chelating agent, forming soluble complexes with calcium thanks to the solubilizing COOH group present in its structure. Such a characteristic of forming soluble complexes with calcium is likely to be of paramount importance, since it avoids the formation and precipitation of microcrystals at the articulation sites, thereby preventing inflammatory reactions from occurring or from going on (Friedman, U.S. Pat. No. 4,244,968 del 13, Jan. 1981). Furthermore, rhein inhibits the formation and release of the superoxide anion from NADPH-dependent biological systems (Mian M. et al. J. Pharm. Pharmacol. 1987; 39: 845–847) and the activity of serine proteases, such as elastase and cathepsin G from man (Raimondi I. et al. Pharmacol. Res. Comm. 1982; 14 (2): 103–112), Zembower D E. et al. J. Med. Chem. 1992; 35: 1597–1605 1992).

Further pharmacological and clinical studies described in literature proved that, in addition to the above mentioned mechanisms, other pathogenetic mechanisms act in the diseases affecting articulations, causing the erosion of the cartilaginous and bone matrix.

Among such mechanisms, the increase in some enzyme activities or an unbalance among the latter and the inhibitors thereof should be stressed. As recently proved by some researchers, cysteine proteases, such as cathepsin B and L, are enzymes strictly connected with the degradation of the cartilage and therefore with the related pathologies. It has widely been reported in literature, that cysteine proteases, cathepsins B and L, are capable of inducing directly or indirectly (by activation of proenzymes), the degradation of the main components of the cartilaginous and bone extracellular matrix (Roughley P J. et al. Biochem. J. 1977; 167; 639–637; Sakamoto S. et al. MOL. Aspects Med. 1988; 10; 299–428; Nguyen P j. et al. Biochem. J. 1991 Aug. 15; 278 (pt 1): 143–7; Maciewiez R A. et al. Biomed. Biochim. Acta 1991; 50 (4–6): 561–4; Buttle D J. Arthritis Rheum. 1993; 36 (12); 1709–17; Pelletier J P. et al. Osteoarthritis 1993; 19 (3); 545–568).

Moreover, the interest in these enzyme activities, has been confirmed by studies carried out on laboratory animals (rats) in which rheumatoid arthritis had been induced. In said animals, the effect of the inhibitors of cysteine proteases, such as fluoromethylketones, on the development of the disease was evaluated particularly on the cartilaginous and bone articular lesions.

The results of said studies showed that the enzyme inhibitors can be clinically valuable in the treatment of arthritis (Ahmed N K. et al. Biochem. Pharmacol. 1992; 44 (6); 1201–7; Meijers M, Billingham M. et al. Agents actions 1993; 39 (1); 219–21; Esser R E. et al. J. Reumatol. 1993; 20 (7); 1176–83).

Other authors (Gabrijelcic D. et al. J. Clin. Chim. Biochem. 1990; 28 (3); 149–53) evidenced the presence of cathepsin B and H in the synovial fluid of patients with different diseases of the articulation whereas Martel-Pelletier J. et al., J. Orthop. (1990): 8 (3:336) proved the existence of an unbalance between the levels of cathepsin B and the inhibitors thereof in the cartilaginous tissue of osteoarthrosic patients.

Huet et al. Arthritis Rheum. (1993): 36 (3): 772 showed that IL-1 and TNF stimulate the activity of cysteine proteases in synovial cells of explants from patients affected with osteoarthrosis and arthritis.

From what stated above, it is clear that cysteine proteases are actively involved in the osteoarthrosic and arthritic pathologies, therefore the use of a therapeutical agent markedly inhibiting the activity of said proteases is widely justified.

Now it has surprisingly been found that anthraquinone mono- and disulfonic acid derivatives have remarkable activity against cysteine proteases.

It is an object of the present invention the use for the preparation of a medicament useful for the treatment of pathologies in which the erosion of the cartilaginous and bone matrix occurs in the most advanced steps of the disease, in particular osteoarthrosis and rheumatoid arthritis, of the compounds of general formula (I)

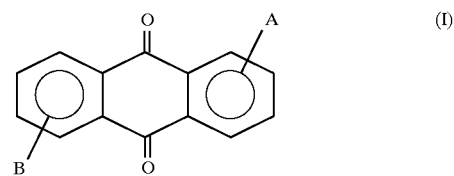

wherein:

A is a group of formula —$SO_3R$, in which R is hydrogen or a cation capable of giving a water-soluble derivative; or A is a group of formula —$SO_2R^1$, wherein $R^1$ is a —$NR^2R^3$ group, in which $R^2$ is hydrogen or $C_1$-$C_6$ straight or branched alkyl, $R^3$ is —CH(COOH)—$R^5$, wherein $R^5$ is $C_1$-$C_6$ alkyl or $C_7$-$C_{12}$ arylalkyl; —$(CH_2)_n$—COOH, wherein n is a integer from 1 to 6, $C_1$-$C_6$ straight or branched alkyl, —$C_6H_4$—O—$(CH_2)_m$—$CH_3$, wherein m is a integer from 1 to 4; or $R^1$ is a —$OR^4$ group, in which $R^4$ is a $C_1$-$C_6$ straight or branched alkyl group or an optionally substituted $C_6$-$C_{10}$ aryl group;

B is a hydrogen atom; or

B has the same meanings as A; with the proviso that A and B are simultaneously —$SO_3R$ or —$SO_2R^1$.

With the expression "a cation capable of giving a water-soluble derivative", those skilled in the art can evaluate which cations are able to play the solubilizing function and, at the same time, to give rise to non-toxic derivatives which do not affect adversely the pharmacological activity of the compounds of formula (I). Examples of said type of cation are metal cations such as lithium, sodium, potassium.

Examples of $C_1$-$C_6$ straight or branched alkyl group are methyl, ethyl, propyl, isopropyl, butyl, isobutyl, tert-butyl, pentyl, hexyl.

Examples of $C_7$-$C_{12}$ arylalkyl group are benzyl, 2-phenylethyl, 1-phenylethyl, 3-phenylpropyl, 1-naphthylmethyl, 2-naphthylmethyl.

Examples of $C_6$-$C_{10}$ group are phenyl, naphthyl. Optional substituents groups can be for example amino, mono- or of-($C_1$-$C_6$)-alkylamino, such as diethylamino, hydroxy, $C_1$-$C_6$ alkoxy, such as isopropoxy, thio.

The following novel compounds according to the present invention are included within the above general formula:
2,6-anthraquinonesulfonamido-N,N-caproic acid;
N,N'-diethyl-2,6-anthraquinonedisulfonamide;
N,N'-(p-ethoxyphenyl)-2,6-anthraquinonedisulfonamide;
bis-2-(2,6-anthraquinonedisulfon)-N,N'-diamidopropionic acid;
bis-2-(2,6-anthraquinonedisulfon)-N,N-diamido-3-phenyl-propionic acid.

Anthraquinone dibasic sulfonamides with antiviral activity have been described by M. Grisar et al. in Journal of Medicinal Chemistry, 1974, vol. 17, n. 8, p. 890–893.

Anthraquinone sulfonamides are described in GB 2025954 to be generally useful as intermediates for dyes, chemical products for agriculture and pharmaceuticals. Particularly, they are described as components of aqueous solutions for removing hydrogen sulfide from gases.

The compounds of the invention can be prepared from anthraquinone mono- and/or disulfonic acid by means of the intermediates:

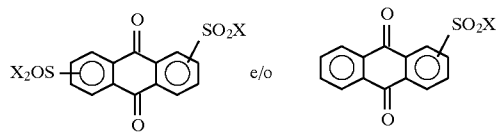

in which X is a halogen, in particular chlorine.

Such an intermediate is known to be prepared reacting mono or disulfonic acid with chlorosulfonic acid or with phosphorous pentachloride or with phosphorous oxychloride or with mixtures of the last two.

The resulting halogenated derivative is reacted with a compound of general formula $HNR^2R^3$.

The technique which can be applied to the latter step varies with the type of $R^2$ and $R^3$, the purity and the obtainable yields. In some cases, the sulfonic acid chloride is reacted with a $HNR^2R^3$ strong excess, whereas in other cases it is preferred to carry out the reaction in a suitable solvent; as examples of appropriate solvents, ethyl ether and methylene chloride can be mentioned. When the presence of a base is suitable, preferred are those such as amines, for example triethylamine and paradimethylaminopyridine.

The reaction conditions depend on the nature of the reagents, the solvent and the presence or the absence of a base as well as its amount, if any. Temperatures range from −10° C. and the solvent boiling point. The most suited operative conditions range from 5° to 30° C. The reaction times vary depending on other parameters, but they usually range from 2 hours to 3 days.

Analogously, the halogenated derivative is reacted with a $R^1OH$ alcohol, wherein $R^1$ is $C_1$-$C_6$ alkyl, thereby obtaining the sulfonic acid ester. The preferred method consists in reacting the sulfonic acid sodium salt with chlorosulfonic acid in excess at room temperature for about 24 hours.

After that, sulfonyl chloride is recovered by filtration, after hydrolysis of the chlorosulfonic acid excess with water and ice. Sulfonyl chloride is reacted with an amine $HNR^1R^2$ or with an alcohol $R^3OH$, in which $R^1$, $R^2$, $R^3$ have the meanings defined above, preferably at room temperature and in the presence of tertiary amines, particularly in when operating in a solvent.

Anthraquinone mono- and disulfonic acids and substituted derivatives of the present invention are remarkably effective in various pharmacological tests.

By way of example, the experimental results of some enzyme tests carried out with mono- and disulfonic derivatives having $SO_3R$ groups at the positions 1,5 and 2,6 are reported (see Tables 1 and 2).

Effects on human cathepsin B and L enzymatic activity

The anthraquinone monosulfonated and disulfonated compounds were dissolved in distilled water whereas the derivatives thereof were dissolved in dimethylsulfoxide. The concentration of the tested product was added to the reaction mixture in a volume of 100 μl.

Composition of the reaction mixture: 0.005M acetate buffer pH 6.0+2 mM cysteine+1 mM EDTA; Enzyme 1 U/ml (cathepsin B or L) (Calbiochem); substrate 0.2 mM Z-Phe-Arg-AMC (Novabiochem) final reaction volume 2 ml; temperature 25° C.; observation time for cathepsin B: 2 minutes; for L: 8 minutes. This is a fluorimetric determination wherein the excitation wavelength was 380 nm, the emission one being instead 460 nm. Fluorescence was read by means of a Perkin-Elmer spectrophotometer mod. LS-3B.

Studied concentrations

Anthraquinone-2,6-disulfonic acid: 1–5–10 μM
Anthraquinone-1,5-disulfonic acid: 1–5–10 μM
N,N'-(p-Ethoxyphenyl)-2,6-anthraquinone-disulfonamide: 1–10 μM.

The results reported in Tables 1 and 2 show that the tested compounds markedly inhibit the activity of cathepsins B and L from humans.

TABLE 1

EFFECT OF ANTHRAQUINONE MONO- AND DISULFONIC ACIDS ON HUMAN CATHEPSIN B ENZYMATIC ACTIVITY

| Compound | Conc. μm | Experiment n. 1 | 2 | 3 | % Inhibition M |
|---|---|---|---|---|---|
| 2,6-anthra- | 10 | 98.9 | 98.2 | 87.7 | 94.9 |
| quinonedisul- | 5 | 68.5 | 65.8 | 76.0 | 70.1 |
| fonic acid | 1 | 43.7 | 33.7 | 38.5 | 40.7 |
| Acid 1,5-an- | 10 | 55.1 | 36.6 | 41.6 | 44.4 |
| thraquinonedi- | 5 | 10.3 | 7.2 | 11.4 | 9.6 |
| sulfonic acid | 1 | 4.1 | 3.6 | 2.5 | 3.4 |
| N,N'-(p-ethoxy- | 10 | 76.6 | 80.6 | 83.4 | 80.2 |
| phenyl)-2,6- | 1 | 23.7 | 18.6 | 14.8 | 19.0 |
| anthraquinone- | | | | | |
| disulfonamide | | | | | |

TABLE 2

EFFECT OF ANTHRAQUINONE MONO- AND DISULFONIC ACIDS ON HUMAN CATHEPSIN L ENZYMATIC ACTIVITY

| Compound | Conc. $\mu$m | Test n. 1 | 2 | 3 | % Inhibition M |
|---|---|---|---|---|---|
| 2,6-anthra-quinonedi-sulfonic acid | 10 | 92.1 | 96.5 | 94.8 | 94.5 |
|  | 1 | 39.6 | 31.4 | 35.8 | 35.6 |
| 1,5-anthra-quinonedi-sulfonic acid | 10 | 48.6 | 60.5 | 53.9 | 54.3 |
|  | 1 | 10.5 | 8.4 | 5.5 | 8.1 |
| N,N'-(p-ethoxy-phenyl)-2,6-anthraquinone-disulfonamide | 10 | 53.6 | 48.1 | 63.8 | 55.2 |
|  | 1 | 8.5 | 7.1 | 10.9 | 8.8 |

Adjuvant arthritis

The test evaluates the effect of the compounds anthraquinone-2,6-disulfonic acid and N,N'-diethylanthraquinone-2,6-disulfonamide on rheumatoid arthritis in the rat induced by administration of complete Freund's adjuvant. Diacetylrhein was used as control.

For the test, albino Sprague Dawley rats weighing 200±10 g, were subdivided into four groups of six animals each. All of the compounds were administered orally at a dosage of 20 mg/kg. Arthritis was induced administering all the animals, in the left rear paw, with 5 mg of Freund's complete adjuvant suspended in 0.05 ml of paraffin oil (prior to the treatment, the paw volume of both rear paws was measured). The treatment with the tested products started 5 days after the arthritis induction and was carried out for ten days. Al the end of this time, the animals were killed to effect the analysis of the following evaluation parameters: measurement of the volume of both left and right rear paws; Rx in lateral and antero-posterior position of the tibio-tarsal articulation of the left paw; histology evaluation of the articulation of both left and right rear paws.

The obtained results show that the compounds anthraquinone-2,6-disulfonic acid and N,N'-diethylanthraquinone-2,6-disulfonamide inhibit by 18.6 and 21.4% respectively the increase in the volume of the left rear paw, whereas diacetylrhein caused an 8.3% reduction. The effect of the two disulfonated compounds on the increase in the volume of the right paw was much more marked. In fact, an inhibition of respectively 67.5 and 62.3% (acid anthraquinone-2,6-disulfonic acid and N,N'-diethylanthraquinone-2,6-disulfonamide) was observed, versus a complete lack in activity by diacetylrhein (see Table 3). Furthermore, radiographies show that the two disulfonated compounds inhibit their loss in bone mass and significantly protect the tibio-tarsal articulation It is indeed evident from the histological examination of the latter, that the disulfonated compounds markedly inhibit the formation of fibrous tissue in the articulation whereas this is remarkably present in the articulation of the control groups and in those treated with diacetylrhein.

TABLE 3

EFFECT OF ANTHRAQUINONE MONO- AND DISULFONIC ACIDS IN THE OEDEMA INDUCED BY FREUND'S COMPLETE ADJUVANT

| Compound | Dose mg/kg/os | Volume increase in the oedema after 15 days | |
|---|---|---|---|
| | | Left paw | Right paw |
| Control | — | 252 ± 26 | 77 ± 29 |
| Acid 2,6-anthraquinonedi-sulfonic acid | 20 | 205 ± 41 | 25 ± 20 |
| N,N'-diethyl-2,6-anthra-quinonedi-sulfonamide | 20 | 198 ± 31 | 29 ± 12 |
| Diacetylrhein | 20 | 231 ± 22 | 92 ± 30 |

Such a protecting activity is also evidenced by the histological examinations carried out on the rat tibio-tarsal articulation.

Contrary to rhein, said products are nor copper neither calcium chelating agents, they do not inhibit the production and the release of the superoxide anion from NADPH-dependent biological systems, do not inhibit the activity of superoxide dismutase, they are not serine proteases inhibitors, they are not mutagenic in the Ames test and cause no chromosomal aberrations as well.

Test of induction of chromosomal aberrations

The clastogenetic effect of rhein and of 2,6-anthraquinonedisulfonic acid, was evaluated using the test of the induction of chromosomal aberrations in cell cultures of chinese hamster ovary (CHO). In this test, the cell line was treated with the tested substances and with suitable controls, in the presence of a metabolic activation system for four hours. After that, the cell in growth exponential phase were treated with colchicine (Colcemid$^R$) for 90 minutes, so as to obtain a significant number of cells in metaphase and to recover them for the preparation of the chromosome suspension. As the positive standard, cyclophosphamide was used (1–5–10–12.5–25 $\mu$g/ml).

The toxicity of the tested compounds was evaluated by means of the assay of the efficiency of plating, treating the cells for four hours, then seeding them at a concentration of 200 cells/5 ml of fresh culture medium.

On the ground of the results obtained by means of this test, dosages were selected for the treatment in the test of induction of chromosomal aberrations, so as not to exceed, with the highest dosage, 50% toxicity levels.

The selected doses were:

rhein: 25–50–100–200 $\mu$g/ml
Acid 2,6-anthraquinonedisulfonic acid: 50–100–150–200–250 $\mu$g/ml.

The chromosomal aberrations were recorded describing the type of structural damage. The numeric aberrations and gaps were discarded. Metaphases showing a good chromosomal opening, a good staining and an acceptable chromosome number (20±2) were selected. For statistical evaluations of the results, the quadratic Chi test was used.

The results prove that the compound 2,6-anthraquinonedisulfonic acid induces no chromosomal aberrations whereas rhein is positive at doses of 100 and 200 $\mu$g/ml (see Tables 4 and 5).

TABLE 4

CHROMOSOMAL ABERRATION ASSAY ON CHINESE HAMSTER OVARY CELLS

| Compound | Dose | Total metaphases | Metaphases with aberrations | P |
|---|---|---|---|---|
| Control + S - 9 | // | 220 | 13 | |
| CPS + S - 9 | 10 µg/ml | 32 | 12 | P < 0.001 |
|  | 5 µg/ml | 100 | 25 | P < 0.001 |
|  | 1 µg/ml | 100 | 10 | N.S. |
| 2,6-anthraquinone sulfonic acid + S - 9 | 250 µg/ml | 100 | 6 | N.S. |
|  | 200 µg/ml | 100 | 8 | N.S. |
|  | 150 µg/ml | 100 | 8 | N.S. |
|  | 100 µg/ml | 100 | 4 | N.S. |
|  | 50 µg/ml | 100 | 2 | N.S. |

CPS = Cyclophosphamide
S - 9 = metabolic activation system

TABLE 5

CHROMOSOMAL ABERRATION ASSAY ON CHINESE HAMSTER OVARY CELLS

| Compound | Dose (µg/ml) | Aberrations simple (S) | Aberrations complex (C) | Aberrations S + C | P |
|---|---|---|---|---|---|
| Control 400 metaphases | // | 8 | 4 | 12 | |
| CPS 100 metaphases | 25 | 0 | 87 | 87 | P < 0.001 |
|  | 12.5 | 0 | 44 | 44 | P < 0.001 |
| Rhein 100 metaphases | 200 | 3 | 5 | 8 | P < 0.05 |
|  | 100 | 3 | 6 | 9 | P < 0.05 |
|  | 50 | 1 | 3 | 4 | N.S. |
|  | 25 | 1 | 1 | 2 | N.S. |

Therefore, such characteristics markedly differentiate the compounds of the invention from rhein.

Action of disulfonated anthraquinone on copper "scavenging" effect

The study involves the production of superoxide anion by means of the hypoxanthine/xanthine oxidase system and the target is the reduction in cytochrome C iron content. Copper is known to be capable of capturing the radical produced by said system. Copper chelants inhibit such a "scavenging" effect.

Table 6 shows that rhein inhibits said effect, whereas the compounds 1-anthraquinonesulfonic acid and 2-anthraquinonesulfonic acid are nearly inactive.

TABLE 6

EFFECT ON COPPER "SCAVENGING" ACTION

| Compound | % Reduction |
|---|---|
| 1-AQ | 3 |
| 2-AQ | 5 |
| 1,5-AQ | 4 |
| 2,6-AQ | 6 |
| rhein | 45 |

1-AQ: anthraquinone-1-sulfonic
2-AQ: anthraquinone-2-sulfonic
1,5-AQ: anthraquinone-1,5-disulfonic acid
2,6-AQ: anthraquinone-2,6-disulfonic acid The present invention also relates to pharmaceutical compositions containing a therapeutically effective amount of a compound of formula I in admixture with conventional carriers and excipients.

The compositions according to the invention are prepared according to known methods, for example as described in "Remington's Pharmaceutical Sciences Handbook", XVII Ed., Mack Pub. Inc., N.Y., U.S.A..

Examples of compositions for the enteral, parenteral, topic administrations are tablets, capsules, granules, controlled-release formulations, liquid drinkable formulations, injectables, suppositories, creams, transdermal formulations.

In the oral formulations, the dosage of the active ingredient will range from 10 to 500 mg depending on the activity of the product and on the therapeutic uses. The systemic use will range from 1 to 100 mg.

In the following, illustrative examples are reported.

EXAMPLE 1

N,N'-Diethyl-2,6-anthraquinonedisulfonamide 13.0 g of anthraquinone-2,6-disulfonylchloride are suspended in 300 ml of methylene chloride, under strong stirring. 300 ml of diethylamine are added thereto, by means of a dropping funnel at such a rate as not to exceed 25°–30° C., cooling, if necessary, the solution. The resulting suspension is stirred for 6 hours, then left to stand overnight. The suspension is then added with 100 ml of 1N NaOH under stirring, stirred for 2 hours and then the resulting solid is filtered, washing it thoroughly with water.

9,3 g of a product with a good purity (95–97% by HPLC) are obtained, which, if necessary, can be recrystallized from a 3/1 dimethylacetamide/water solution.

IR and NMR analysis confirm the identity of the product.

EXAMPLE 2

N,N'-(p-Ethoxyphenyl)-2,6-anthraquinonedisulfonamide 15.5 ml of p-phenetidine are added to 150 ml of methylene chloride, under strong stirring. 6.1 g of anthraquinone-2,6-disulfonylchloride are gradually added, in small portions, so as not to exceed 15°–20° C., cooling, if necessary, the solution. The resulting suspension is stirred for 3 hours, then left to stand for 3 days; the obtained solid is filtered, washing thoroughly with 1M hydrochloric acid and then with water. 9.8 g of a product are obtained, which is recrystallized twice from dimethylacetamide/water solutions. Finally 3,8 g of the pure product are obtained.

IR and NMR analysis confirm the identity of the product.

EXAMPLE 3

2,6-Anthraquinonedisulfonamido-N,N'-caproic acid 16.4 g of methyl-6-aminocaproate hydrochloride, 18 ml of triethylamine and 200 mg of p-dimethyl-aminopyridine are added to 150 ml of diethyl ether, stirring the whole thoroughly. 6.1 g of anthraquinone-2,6-disulfonylchloride are gradually added, in small portions, so as not to exceed 15°–20° C., cooling, if necessary, the solution. The resulting suspension is stirred for 3 hours at room temperature, then 3 hours under reflux, then it is left to stand overnight; after that the solvent is evaporated off and the obtained solid is taken up with 35 g of KOH dissolved in 500 ml of water/methanol 1/1. The mixture is stirred for 1 hour at room temperature, then is acidified with 20% hydrochloric acid to markedly acidic pH; after stirring for 5 minutes the resulting solid is filtered, washing it thoroughly with water. 5.0 g of a product are obtained, which is recrystallized twice from dimethylacetamide/water solutions. Finally 2.1 g of the pure product are obtained.

IR and NMR analysis confirm the identity of the product.

EXAMPLE 4

Soft gelatin capsules:
Each soft gelatin capsule contains:

|  | 1) | 2) |
|---|---|---|
| Active ingredient | 100 mg | 300 mg |
| Soy oil | 50 mg | 150 mg |

The dispersion of the active ingredient in soy oil is dosed in soft gelatin capsules using the suitable device.

The active ingredients used in this formulation are preferably:
1) —N,N'-diethyl-2,6-anthraquinonedisulfonamide
2) —N,N'-(p-ethoxyphenyl)-2,6-anthraquinonedisulfonamide.

EXAMPLE 5

Hard gelatin capsules
Each capsule contains:

| Active ingredient | 40 mg | 200 mg |
|---|---|---|
| Lactose | 200 mg | 285 mg |
| Magnesium stearate | 10 mg | 15 mg |

The products are mixed and then dosed in capsules of suitable size.

The active ingredients used in this formulation are preferably selected from:
2,6- or 1,5-anthraquinonedisulfonic acid sodium salts;
2,6-anthraquinonedisulfonamido-N,N'-caproic acid.

EXAMPLE 6

Tablets
Each tablet contains:

| Active ingredient | 250 mg | 15 mg |
|---|---|---|
| Microcrystalline cellulose | 200 mg | 800 mg |
| Anhydrous lactose | 220 mg | 97 mg |
| Sodium carboxymethyl starch | 21 mg | 6 mg |
| Magnesium stearate | 9 mg | 2 mg. |

The active ingredient is mixed thoroughly with microcrystalline cellulose and the anhydrous lactose, sodium carboxymethyl starch and magnesium stearate are added mixing again, then the resulting mixture is sieved and tabletted to obtain tablets weighing 700 and 920 mg respectively.

The active ingredients used in this formulation are preferably:
1)—N,N-diethyl-2,6-anthraquinonedisulfonamide
2)—N,N-(p-ethoxyphenyl)-2,6-anthraquinonedisulfonamide
3)—anthraquinonesulfonic acid of formula (I) sodium salts.

EXAMPLE 7

Cream

| Active ingredient | 2.000 g |
|---|---|
| Mixture of cetyl and stearyl alcohols | 15.000 g |

-continued

Cream

| Sodium lauryl sulfate | 1.500 g |
|---|---|
| Decyl oleate | 10.000 g |
| Vaselin oil | 5.000 g |
| Depurated water | 66.000 g |
| Methyl-p-oxy-benzoate | 0.160 g |
| Propyl para-oxy-benzoate | 0.040 g |
| Rose essence | 0.300 g |

The mixture of cetyl and stearyl alcohols is melted with sodium laurylsulfate and decyl oleate, adding the active ingredient and mixing thoroughly. The obtained product is then added to water, brought to the same temperature at which methyl-p-oxybenzoate and propyl-p-oxybenzoate had been dissolved, emulsified carefully in a suitable device, cooled to about 60° C. under stirring, added with the rose essence and then cooled and distributed in suitable containers.

Particularly suitable active ingredients of the preparations are:
—N,N'-diethyl-2,6-anthraquinonedisulfonamide;
—N,N'-(p-ethoxyphenyl)-2,6-anthraquinonedisulfonamide.

EXAMPLE 8

Ointment

With similar procedures, ointments can be prepared with active ingredients consisting of the salts of the compounds of formula (I) using compositions of the following type:

| Active ingredient | 3.000 g |
|---|---|
| Hamamelis water | 27.000 g |
| Cetyl alcohol | 16.500 g |
| Free and esterified sterols | 1.000 g |
| Methyl p-oxybenzoate | 0.150 g |
| Propyl gallate | 0.030 g |
| Propylene glycol | 7.000 g |
| Rose essence | 0.250 g |
| Disodium versenate | 0.050 g |
| Vitamin F 80% | 1.250 g |
| Polyglycol esters of saturated and unsaturated fatty amides $C_{13}$–$C_{20}$ | 0.500 g |
| Depurated water q.s. to 100 g. | |

EXAMPLE 9

Intramuscular vials

Each vial contains:

| Active ingredient | 25.00 g |
|---|---|
| Sodium chloride | 3.80 g |
| Sodium citrate dihydrate | 25.73 g |
| Citric acid monohydrate | 7.87 g |
| Water for injectable preparations | q.s. to 2 ml. |

The solution of the active ingredient and of the excipients is filtered sterilely and partitioned in vials which are subsequently sterilized in autoclave at 121° C. for 15 minutes.

The active ingredients used in this formulation are preferably the anthraquinonesulfonic acid of formula (I) sodium salts.

EXAMPLE 10

Intra-articular vials
Each vial of freeze-dried product contains

| Active ingredient | 1 mg |
|---|---|
| Mannitol | 50 mg |
| Sodium hydroxide | q.s. to pH 6.5 |

Each solvent vial contains
Water for injectable preparations 2 ml.

The solution of the active ingredient and of the excipients is sterilely filtered and partitioned in vials, then freeze-dried in a suitable device.

The active ingredients used in this formulation are preferably the anthraquinonesulfonic acid of formula (I) sodium salts.

I claim:

1. A method of treatment of pathologies wherein the erosion of the cartilaginous and bone matrix occurs in the most advanced steps of the disease comprising administering a treatment effective amount of a compound of formula (I):

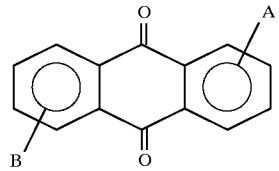

wherein:

A is a group of formula —$SO_3R$, in which R is hydrogen or a cation capable of giving a water-soluble derivative;
or A is a group of formula —$SO_2R^1$, wherein $R^1$ is a —$NR^2R^3$ group, in which $R^2$ is hydrogen or $C_1$-$C_6$ straight or branched alkyl, $R^3$ is —CH(COOH)—$R^5$, wherein $R^5$ is $C_1$-$C_6$ alkyl or $C_7$-$C_{12}$ arylalkyl; —$(CH_2)_n$—COOH, wherein n is an integer from 1 to 6, $C_1$-$C_6$ straight or branched alkyl, —$C_6H_4$—O—$(CH_2)m$—$CH_3$, wherein m is an integer from 1 to 4;
or R' is a —$OR^4$ group, in which $R^4$ is a $C_1$-$C_6$ straight or branched alkyl group or an optionally substituted $C_6$-$C_{10}$ aryl group;

B is a hydrogen atom;
or

B has the same meanings as A; with the proviso that A and B are simultaneously —$SO_3R$ or —$SO_2R^1$.

2. The method according to claim 1, wherein the pathology is osteoarthrosis.

3. The method according to claim 1, wherein the pathology is arthritis.

4. The method according to claim 1, wherein the compound is selected from the group consisting of:

2,6-anthraquinonesulfonamido-N,N-caproic acid;

N,N'-diethyl-2,6-anthraquinonedisulfonamide;

N,N'-(p-ethoxyphenyl)-2,6-anthraquinonedisulfonamide;

bis-2-(2,6-anthraquinonedisulfon)-N,N'-diamido propionic acid;

bis-2-(2,6-anthraquinonedisulfon)-N,N-diamido-3-phenyl-propionic acid.

5. A compound selected from the group consisting of:

2,6-anthraquinonesulfonamido-N,N-caproic acid;

N,N'-diethyl-2,6-anthraquinonedisulfonamide;

N,N'-(p-ethoxyphenyl)-2,6-anthraquinonedisulfonamide;

bis-2-(2,6-anthraquinonedisulfon)-N,N'-diamido propionic acid;

bis-2-(2,6-anthraquinonedisulfon)-N,N-diamido-3-phenylpropionic acid.

6. A process for the preparation of the compounds of claim 5, comprising the reaction of the corresponding anthraquinone mono- or disulfonic acid halide with an amine.

7. Pharmaceutical compositions containing a therapeutically effective amount of a compound of claim 1, in admixture with pharmaceutically acceptable carriers and excipients.

* * * * *